(12) United States Patent
Ladet et al.

(10) Patent No.: US 9,511,175 B2
(45) Date of Patent: *Dec. 6, 2016

(54) MEDICAL DEVICES WITH AN ACTIVATED COATING

(71) Applicants: Sofradim Production, Trévoux (FR); Covidien LP, Mansfield, MA (US)

(72) Inventors: Sébastien Ladet, Caluire et Cuire (FR); Ahmad Robert Hadba, Fort Worth, TX (US)

(73) Assignees: Sofradim Production, Trevoux (FR); Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/054,652

(22) Filed: Feb. 26, 2016

(65) Prior Publication Data

US 2016/0175490 A1 Jun. 23, 2016

Related U.S. Application Data

(62) Division of application No. 13/202,390, filed as application No. PCT/IB2010/000665 on Feb. 22, 2010, now Pat. No. 9,273,191.

(60) Provisional application No. 61/154,383, filed on Feb. 21, 2009.

(51) Int. Cl.
| | |
|---|---|
| A61L 33/00 | (2006.01) |
| A61L 31/10 | (2006.01) |
| A61L 17/14 | (2006.01) |
| A61L 29/08 | (2006.01) |
| C08J 7/04 | (2006.01) |
| A61L 31/16 | (2006.01) |
| B05D 1/00 | (2006.01) |

(52) U.S. Cl.
CPC ............. *A61L 31/10* (2013.01); *A61L 17/145* (2013.01); *A61L 29/085* (2013.01); *A61L 31/16* (2013.01); *B05D 1/00* (2013.01); *C08J 7/047* (2013.01); *A61L 2300/606* (2013.01); *A61L 2420/02* (2013.01)

(58) Field of Classification Search
CPC ...... A61L 17/145; A61L 29/085; A61L 31/10; A61L 31/16; A61L 2300/606; A61L 2420/02; C08J 7/047; B05D 1/00; C08L 101/02
See application file for complete search history.

(56) References Cited

U.S. PATENT DOCUMENTS

| | | | |
|---|---|---|---|
| 3,767,085 A | 10/1973 | Cannon et al. | |
| 4,326,532 A | 4/1982 | Hammar | |
| 4,359,049 A | 11/1982 | Redl et al. | |
| 4,464,321 A | 8/1984 | Pittalis et al. | |
| 4,538,920 A | 9/1985 | Drake | |
| 4,753,536 A | 6/1988 | Spehar et al. | |
| 4,839,345 A | 6/1989 | Doi et al. | |
| 4,857,403 A | 8/1989 | De Lucca et al. | |
| 4,880,662 A | 11/1989 | Habrich et al. | |
| 5,021,207 A | 6/1991 | De Lucca et al. | |
| 5,372,585 A | 12/1994 | Tiefenbrun et al. | |
| 5,455,308 A | 10/1995 | Bastiaansen | |
| 5,562,946 A | 10/1996 | Fofonoff et al. | |
| 5,578,662 A | 11/1996 | Bennett et al. | |
| 5,582,955 A | 12/1996 | Keana et al. | |
| 5,612,050 A | 3/1997 | Rowe et al. | |
| 5,804,318 A | 9/1998 | Pinchuk et al. | |
| 5,911,942 A | 6/1999 | Fofonoff et al. | |
| 6,099,563 A | 8/2000 | Zhong | |
| 6,107,365 A | 8/2000 | Bertozzi et al. | |
| 6,107,453 A | 8/2000 | Zuccato et al. | |
| 6,312,725 B1 | 11/2001 | Wallace et al. | |
| 6,342,591 B1 | 1/2002 | Zamora et al. | |
| 6,451,032 B1 | 9/2002 | Ory et al. | |
| 6,534,611 B1 | 3/2003 | Darling et al. | |
| 6,552,103 B1 | 4/2003 | Bertozzi et al. | |
| 6,570,040 B2 | 5/2003 | Saxon et al. | |
| 6,576,000 B2 | 6/2003 | Carrison | |
| 6,624,245 B2 | 9/2003 | Wallace et al. | |
| 6,881,766 B2 | 4/2005 | Hain | |
| 6,958,212 B1 | 10/2005 | Hubbell et al. | |
| 7,012,126 B2 | 3/2006 | Matsuda et al. | |
| 7,105,629 B2 | 9/2006 | Matsuda et al. | |
| 7,122,703 B2 | 10/2006 | Saxon et al. | |
| 7,144,976 B2 | 12/2006 | Matsuda et al. | |
| 7,172,877 B2 | 2/2007 | Ting | |
| 7,247,692 B2 | 7/2007 | Laredo | |
| 7,294,357 B2 | 11/2007 | Roby | |
| 7,371,719 B2 | 5/2008 | Stupp et al. | |
| 7,375,234 B2 | 5/2008 | Sharpless et al. | |
| 7,560,588 B2 | 7/2009 | Breitenkamp et al. | |

(Continued)

FOREIGN PATENT DOCUMENTS

| | | |
|---|---|---|
| BE | 1008260 A6 | 2/1996 |
| EP | 0490854 A2 | 6/1992 |

(Continued)

OTHER PUBLICATIONS

D Shi, et al., "The Immobilization of Proteins on Biodegradable Polymer Fibers via Click Chemistry", Biomaterials, 29, (2008), pp. 1118-1126.

(Continued)

*Primary Examiner* — Suzanne Ziska

(57) ABSTRACT

Implantable medical devices include a substrate having applied thereto a coating including a polymeric material possessing a core and at least one functional group known to have click reactivity.

18 Claims, No Drawings

(56) References Cited

U.S. PATENT DOCUMENTS

| | | |
|---|---|---|
| 7,618,944 B2 | 11/2009 | Breitenkamp et al. |
| 7,638,558 B2 | 12/2009 | Breitenkamp et al. |
| 7,667,012 B2 | 2/2010 | Saxon et al. |
| 7,795,355 B2 | 9/2010 | Matyjaszewski et al. |
| 7,807,619 B2 | 10/2010 | Bertozzi et al. |
| 7,981,444 B2 | 7/2011 | Tomalia et al. |
| 7,985,424 B2 | 7/2011 | Tomalia et al. |
| 8,034,396 B2 | 10/2011 | Kapiamba et al. |
| 8,968,818 B2 * | 3/2015 | Belcheva ................ A61L 31/04 427/2.24 |
| 9,273,191 B2 | 3/2016 | Ladet et al. |
| 2002/0016003 A1 | 2/2002 | Saxon et al. |
| 2002/0161170 A1 | 10/2002 | Matsuda et al. |
| 2002/0169275 A1 | 11/2002 | Matsuda et al. |
| 2002/0173616 A1 | 11/2002 | Matsuda et al. |
| 2003/0100086 A1 | 5/2003 | Yao et al. |
| 2003/0135238 A1 | 7/2003 | Milbocker |
| 2003/0162903 A1 | 8/2003 | Day |
| 2003/0199084 A1 | 10/2003 | Saxon et al. |
| 2003/0205454 A1 | 11/2003 | Hlavinka et al. |
| 2004/0170752 A1 | 9/2004 | Luthra et al. |
| 2004/0185053 A1 | 9/2004 | Govindan |
| 2004/0209317 A1 | 10/2004 | Ting |
| 2004/0249438 A1 | 12/2004 | Lefranc et al. |
| 2005/0032081 A1 | 2/2005 | Ju et al. |
| 2005/0038472 A1 | 2/2005 | Furst |
| 2005/0148032 A1 | 7/2005 | Saxon et al. |
| 2005/0222427 A1 | 10/2005 | Sharpless et al. |
| 2005/0233389 A1 | 10/2005 | Ting et al. |
| 2005/0244453 A1 | 11/2005 | Stucke et al. |
| 2006/0018948 A1 | 1/2006 | Guire et al. |
| 2006/0036022 A1 | 2/2006 | Callaghan et al. |
| 2006/0085033 A1 | 4/2006 | Criscuolo et al. |
| 2006/0108393 A1 | 5/2006 | Heinrich et al. |
| 2006/0110782 A1 | 5/2006 | Bertozzi et al. |
| 2006/0142404 A1 | 6/2006 | Berge et al. |
| 2006/0147963 A1 | 7/2006 | Barone et al. |
| 2006/0193865 A1 | 8/2006 | Govindan |
| 2006/0228300 A1 | 10/2006 | Chang et al. |
| 2006/0228357 A1 | 10/2006 | Chang et al. |
| 2006/0240092 A1 | 10/2006 | Breitenkamp et al. |
| 2006/0276658 A1 | 12/2006 | Saxon et al. |
| 2007/0020620 A1 | 1/2007 | Finn et al. |
| 2007/0037964 A1 | 2/2007 | Saxon et al. |
| 2007/0060658 A1 | 3/2007 | Diaz et al. |
| 2007/0077564 A1 | 4/2007 | Roitman et al. |
| 2007/0086942 A1 | 4/2007 | Chang et al. |
| 2007/0087001 A1 | 4/2007 | Taylor et al. |
| 2007/0099251 A1 | 5/2007 | Zhang et al. |
| 2007/0140966 A1 | 6/2007 | Chang et al. |
| 2007/0178133 A1 | 8/2007 | Rolland |
| 2007/0178448 A1 | 8/2007 | Tsao et al. |
| 2007/0190597 A1 | 8/2007 | Agnew et al. |
| 2007/0212267 A1 | 9/2007 | Organ et al. |
| 2007/0244265 A1 | 10/2007 | Matyjaszewski et al. |
| 2007/0244296 A1 | 10/2007 | Tomalia et al. |
| 2007/0249014 A1 | 10/2007 | Agnew et al. |
| 2007/0254006 A1 | 11/2007 | Loose et al. |
| 2007/0258889 A1 | 11/2007 | Douglas et al. |
| 2007/0269369 A1 | 11/2007 | Gegg et al. |
| 2007/0272122 A1 | 11/2007 | Lahann et al. |
| 2007/0275387 A1 | 11/2007 | Ju |
| 2007/0298006 A1 | 12/2007 | Tomalia et al. |
| 2008/0015138 A1 | 1/2008 | Hamilton et al. |
| 2008/0021486 A1 | 1/2008 | Oyola et al. |
| 2008/0035243 A1 | 2/2008 | Breitenkamp et al. |
| 2008/0038472 A1 | 2/2008 | Suzuki et al. |
| 2008/0045686 A1 | 2/2008 | Meagher et al. |
| 2008/0050731 A1 | 2/2008 | Agnew et al. |
| 2008/0051562 A1 | 2/2008 | Chaikof et al. |
| 2008/0103564 A1 | 5/2008 | Burkinshaw et al. |
| 2008/0121657 A1 | 5/2008 | Voegele et al. |
| 2008/0138317 A1 | 6/2008 | Fung |
| 2008/0160017 A1 | 7/2008 | Baker et al. |
| 2008/0166363 A1 | 7/2008 | Govindan et al. |
| 2008/0171067 A1 | 7/2008 | Govindan et al. |
| 2008/0187956 A1 | 8/2008 | Carrico et al. |
| 2008/0199736 A1 | 8/2008 | Gadeken et al. |
| 2008/0200628 A1 | 8/2008 | Gadeken et al. |
| 2008/0207913 A1 | 8/2008 | Breitenkamp et al. |
| 2008/0214436 A1 | 9/2008 | Yu et al. |
| 2008/0214801 A1 | 9/2008 | Saxon et al. |
| 2008/0214831 A1 | 9/2008 | Sharpless et al. |
| 2008/0221043 A1 | 9/2008 | Harth et al. |
| 2008/0241856 A1 | 10/2008 | Wong et al. |
| 2008/0241892 A1 | 10/2008 | Roitman et al. |
| 2008/0242171 A1 | 10/2008 | Huang et al. |
| 2008/0248126 A1 | 10/2008 | Cheng et al. |
| 2008/0267878 A1 | 10/2008 | Robillard et al. |
| 2008/0283572 A1 | 11/2008 | Boyden et al. |
| 2008/0311412 A1 | 12/2008 | Fokin et al. |
| 2008/0317861 A1 | 12/2008 | Guan |
| 2009/0012457 A1 | 1/2009 | Childers et al. |
| 2009/0018646 A1 | 1/2009 | Zhao |
| 2009/0027603 A1 | 1/2009 | Samulski et al. |
| 2009/0038701 A1 | 2/2009 | Delmotte |
| 2009/0053139 A1 | 2/2009 | Shi et al. |
| 2009/0054619 A1 | 2/2009 | Baker et al. |
| 2009/0061010 A1 | 3/2009 | Zale et al. |
| 2009/0069561 A1 | 3/2009 | Fokin et al. |
| 2009/0082224 A1 | 3/2009 | Haddleton et al. |
| 2009/0098175 A1 | 4/2009 | Buehrer et al. |
| 2009/0099108 A1 | 4/2009 | Jones |
| 2009/0124534 A1 | 5/2009 | Reineke |
| 2009/0137424 A1 | 5/2009 | Tsao et al. |
| 2009/0181402 A1 | 7/2009 | Finn et al. |
| 2009/0182151 A1 | 7/2009 | Wu et al. |
| 2009/0202433 A1 | 8/2009 | Chang et al. |
| 2009/0203131 A1 | 8/2009 | Reineke et al. |
| 2009/0214755 A1 | 8/2009 | Armani et al. |
| 2009/0220607 A1 | 9/2009 | Kiser et al. |
| 2009/0240030 A1 | 9/2009 | Ju et al. |
| 2009/0247651 A1 | 10/2009 | Kapiamba et al. |
| 2009/0250588 A1 | 10/2009 | Robeson et al. |
| 2009/0253609 A1 | 10/2009 | Fleury et al. |
| 2009/0259016 A1 | 10/2009 | Johnson et al. |
| 2009/0263468 A1 | 10/2009 | McAnulty et al. |
| 2009/0269277 A1 | 10/2009 | Chang et al. |
| 2009/0281250 A1 | 11/2009 | DeSimone et al. |
| 2009/0297609 A1 | 12/2009 | Shoichet et al. |
| 2009/0306310 A1 | 12/2009 | Wu et al. |
| 2009/0312363 A1 | 12/2009 | Bradner et al. |
| 2009/0325292 A1 | 12/2009 | Baker et al. |
| 2010/0011472 A1 | 1/2010 | Hugel et al. |
| 2010/0015046 A1 | 1/2010 | Govindan et al. |
| 2010/0021391 A1 | 1/2010 | Douglas et al. |
| 2010/0034862 A1 | 2/2010 | Laronde et al. |
| 2010/0047258 A1 | 2/2010 | Wang et al. |
| 2010/0048738 A1 | 2/2010 | Fleury et al. |
| 2010/0069578 A1 | 3/2010 | Faust et al. |
| 2010/0098640 A1 | 4/2010 | Cohen et al. |
| 2010/0104589 A1 | 4/2010 | Govindan et al. |
| 2010/0121022 A1 | 5/2010 | Musa et al. |
| 2010/0159508 A1 | 6/2010 | Yang et al. |
| 2010/0247433 A1 | 9/2010 | Tirrell et al. |
| 2010/0286405 A1 | 11/2010 | Fokin et al. |
| 2010/0291171 A1 | 11/2010 | Crescenzi et al. |
| 2010/0303754 A1 | 12/2010 | Turpin et al. |
| 2011/0008251 A1 | 1/2011 | Chang et al. |
| 2011/0052696 A1 | 3/2011 | Hult et al. |
| 2011/0060107 A1 | 3/2011 | Matyjaszewski et al. |
| 2011/0143435 A1 | 6/2011 | Stayton et al. |
| 2011/0177156 A1 | 7/2011 | Szoka, Jr. et al. |
| 2011/0183417 A1 | 7/2011 | Reineke |
| 2011/0213123 A1 | 9/2011 | Bertozzi et al. |
| 2011/0257343 A1 | 10/2011 | Harth et al. |
| 2015/0157769 A1 * | 6/2015 | Belcheva ................ A61L 31/04 521/143 |

FOREIGN PATENT DOCUMENTS

| | | |
|---|---|---|
| EP | 1790702 A1 | 5/2007 |
| EP | 1795563 A1 | 6/2007 |
| EP | 1975230 A1 | 10/2008 |

(56) References Cited

FOREIGN PATENT DOCUMENTS

| EP | 2014308 A2 | 1/2009 |
|---|---|---|
| EP | 2090592 A1 | 8/2009 |
| WO | 2006012569 A1 | 2/2006 |
| WO | 2007041394 A2 | 4/2007 |
| WO | 2007121055 A1 | 10/2007 |
| WO | 2008013618 A1 | 1/2008 |
| WO | 2008017029 A2 | 2/2008 |
| WO | 2008075955 A2 | 6/2008 |
| WO | 2008077406 A2 | 7/2008 |
| WO | 2008108736 A1 | 9/2008 |
| WO | 2008115694 A2 | 9/2008 |
| WO | 2008120016 A1 | 10/2008 |
| WO | 2010095049 A1 | 8/2010 |

OTHER PUBLICATIONS

Jerome, et al., "Recent Advances in the Synthesis of Aliphatic Polyesters Ring-Opening Polymerization", Advanced Drug Delivery Reviews, 60, (2008), pp. 1056-1076.

Zhang, et al., "2-Azido-2-deoxycellulose: Synthesis and 1, 3-Dipolar Cycloaddition", Helvetica Chimica Acta, vol. 91, pp. 608-611 (2008).

R. Riva, et al., "Contribution of "Click Chemistry" to the Synthesis of Antimicrobial Aliphatic Copolyester", Polymer 49, (2008), pp. 2023-2028.

Baskin, et al., "Copper Free Click Chemistry for Dynamic In Vivo Imaging", PNAS, vol. 104, No. 43, (Oct. 23, 2007), pp. 16793-16797.

Codelli, et al., "Second Generation Difluorinated Cyclooctynes for Copper-Free Click Chemistry", J. Am. Chem. Soc., vol. 130, No. 34, (2008), pp. 11486-11493.

Sletten and Bertozzi, "A Hydrophilic Azacyclooctyne for Cu-free Click Chemistry", Org. Lett. (2008) 10(14), pp. 3097-3099.

Cazalis, et al., "C-Terminal Site-Specific PEGylation of a Truncated Thrombomodulin Mutant with Retention of Full Bioactivity", Bioconjugate Chem., (2004), 15, pp. 1005-1009.

Haridas, et al., "Design and Synthesis of Triazole-based Peptidedendrimers" Tetrahedron Letters, vol. 48, (2007), pp. 4719-4722.

Raghavan, et al., "Chemical Probes for Profiling Fatty Acid-associated Proteins in Living Cells", Bioorg. Med. Chem. Lett., 18 (2008), pp. 5982-5986.

LeDevedec, et al., "Separation of Chitosan Oligomers by Immobilized Metal Affinity Chromatography", Journal of Chromatography A., 2008, 1194(2), pp. 165-171.

Hartgerink, et al., "Peptide-amphiphile Nanofibers: A Versatile Scaffold for the Preparation of Self Assembling Materials", PNAS, 2002; 99(2), pp. 5133-5138.

Van Berkel, et al., "Metal-Free Triazole Formation as a Tool for Bioconjugation" Chem Bio Chem, 8, (2007), pp. 1504-1508.

Nottelet, et al., Synthesis of an X-ray opaque biodegradable copolyester by chemical modification of poly (.epsilon.-caprolactone) Biomaterials, 27, (2006), pp. 4943-4954.

Smith, et al., "Synthesis and Convenient Functionalization of Azide-labeled Diacyglycerol Analogues for Modular Access to Biologically Active Lipid Probes", Bioconjugate Chem, 19(9), (2008). pp. 1855-1863.

Skierka, et al., "The Influence of Different Acids and Pepsin on the Extractability of Collagen From the Skin of Baltic Cod (*Gadus morhua*)", Food Chemisty, 105, (2007), pp. 1302-1306.

Eastoe, "The Amino Acid Composition of Mammalian Collagen and Gelatin", vol. 61, (1955), pp. 589-600.

Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.

Laughlin, et al., "In Vivo Imaging of Membrane-Associated Glycans in Developing Zebrafish", Science, 320, (2008), pp. 664-667.

Worch and Wittmann, "Unexpected Formation of Complex Bridged Tetrazoles via Intramolecular 1,3-dipolar Cycloaddition of 1,2-0-cyanoallcylidene Derivatives of 3-azido-3-deoxy-D-allose", Carbohydrate Research, 343, (2008), pp. 2118-2129.

Witczak et al., "A Click Chemistry Approach to Glycomimetics: Michael addition of 2,3,4,6-tetra-O-acetyl-1-thio-.beta.-D-glucopyranose to 4-deoxy-1,2-O-isopropylident-L-glycero-pent-4-enopyranos-3-ulose-a convenient route to novel4-deoxy-(1.fwdarw. 5)-5-C-thiodisaccharides", Carbohydrate Research, 342, (2007), 1929-1933.

Marra, et al., "Validation of the Copper(1)-Catalyzed Azide-Alkyne Coupling in Ionic Liquids, Synthesis of a Triazole-Linked C-Disaccharide as a Case Study", J. Org. Chem (2008), 73(6), pp. 2458-2461.

Srinivasachari, et al., "Versatile Supramolecular pDNA Vehicles via "Click Polymerization" of .beta.-cyclodextrin with oligoethyleneamines", Biomaterials, 30, (2009), pp. 928-938.

Arora, et al., "A Novel Domino-click Approach for the Synthesis of Sugar Based Unsymmetrical bis-1,2,3-triazoles", Carbohydrate Research, 343, (2008), 139-144.

Chen, et al., "Synthesis of a C.sub.3-symmetric (1.fwdarw.6)-N-acetylbeta.-D-glucosamine Octadecasaccharide using Click Chemistry", Carbohydrate Research, 340, (2005), pp. 2476-2482.

Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045.

Srinivasachari, etal., "Effects of Trehalose Click Polymer Length on pDNA Complex Stability and Delivery Efficacy", Biomaterials, 28, (2007), pp. 2885-2898.

Godeau, et al., Lipid-Conjugated Oligonucleotides via "Click Chemistry" Efficiently Inhibit Hepatitis C Virus Translation, J. med. Chem., 2008, 51(15), pp. 2374-4376.

Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.

Cantel, et al., "Synthesis and Conformational Analysis of a Cyclic Peptide Obtained via i to i+4 Intramolecular Side-chain to Side-chain Azide-Alkyne 1,3-Dipolar Cycloaddition" J. Org. Chem., 2008, 73 (15), pp. 5663-5614.

Dijk, et al., "Synthesis of Peptide-Based Polymers by Microwave-Assisted Cycloaddition Backbone Polymerization," Biomacro molecules, 2007, 8(2), pp. 327-330.

Koster, et al., "Spectroscopic and Electrochemical Studies of Ferroceryl Triazole Amino Acid and Peptide Bioconjugates Synthesized by Click Chemistry", Organometallics, 2008, 27(23) pp. 6326-6332.

Dijk, et al., "Synthesis and Characterization of Biodegradable Peptide-Baed Polymers Prepared by Microwave-Assisted Click Chemisty", Biomacromolecules, 2008, 9(10), pp. 2834-2843.

Jiang, et al., "Amphiphilic PEG/alkyl-grafted comb polylactides", J. Polymer Science Part B: Polymer Physics, 45(22), 2007, pp. 5227-5236.

Ochs, et al., "Low-Fouling, Biofunctionalized, and Biodegradable Click Capsules", Biomacromolecules, 2008, 9(12), pp. 3389-3396.

Beatty and Tirrell, "Two-color Labeling of Temporally Defined Protein Populations in Mammalian Cells", Bioorg. Med. Chem. Lett., 18 (2008), pp. 5995-5999.

Kolb, et al., "Click Chemistry: Diverse Chemical Function from a Few Good Reactions", Angewandte Chemie, International Edition, Jun. 2001, pp. 2004-2021.

Krouit, et al., "Cellulose surface grafting with polycaprolactone by heterogeneous click-chemistry", European Polymer Journal 44, Dec. 2008, pp. 4074-4081.

Nandivada, et al. Reactive polymer coatings that 'Click'.", Angewandte Chemie, International Edition 45, Apr. 2006, pp. 3360-3363.

Ossipov and Hilborn, Poly(vinyl alcohol)-Based Hydrogels Formed by "Click Chemistry", Macromelecules 2006, 39, pp. 1709-1718.

Binder and Sachsenhofer, "Click Chemistry in Polymer and Materials Science", Macromolecular Rapid Commun. 2007, 28, pp. 15-54.

(56) References Cited

OTHER PUBLICATIONS

Australian Examination Report, Application No. 2010215203 dated May 23, 2014.

* cited by examiner

MEDICAL DEVICES WITH AN ACTIVATED COATING

CROSS-REFERENCE TO RELATED APPLICATIONS

This application is a divisional of U.S. patent application Ser. No. 13/202,390 filed Oct. 13, 2011, which is a National Stage Application of PCT/IB2010/000665 filed Feb. 22, 2010, which claims benefit of and priority to U.S. Provisional Application No. 61/154,383 filed Feb. 21, 2009, and the disclosures of each of the above-identified applications are hereby incorporated by reference in their entirety.

BACKGROUND

Technical Field

The present disclosure relates to implantable devices having coating that imparts an activated surface to the device.

Background of Related Art

Methods for making monofilaments that are suitable to fabricate surgical articles, such as sutures, generally include the steps of extruding at least one bioabsorbable or nonbioabsorbable polymer to provide filaments, drawing or stretching the solidified filaments to achieve molecular orientation, and annealing the drawn filaments to relieve internal stresses.

Various spinning methods may be employed, such as melt spinning, gel spinning, wet or dry spinning, and reaction spinning. Melt spinning uses heat and potentially shear to melt the fiber-forming polymer to a viscosity suitable for extrusion through the die or spinneret. After exiting the die, the fiber solidifies by cooling in air or a suitable chilled fluid bath. In solvent spinning, the fiber-forming polymer is dissolved in a suitable organic solvents or solvent mixture to result in a fluid with suitable viscosity for extrusion through a spinneret. The difference between wet and dry spinning is the means by which the fiber solidifies. In dry spinning, the fiber solidifies as the solvent evaporates under a stream of air or inert gas. In wet spinning, the fiber forms by precipitating from solution as a result of dilution in a non-solvent bath or chemical reaction with a crosslinker in the solvent bath. Gel spinning refers to a process similar to solvent spinning except that the polymer is not fully dissolved in the solvent—a high polymer content is used in the process. The chains of the partially solvated polymer are aligned by the shear during the extrusion process. The filaments are further drawn as they are passed through a gas drying then a wet precipitating bath. The resulting fibers have an unusually high degree of alignment and high tensile strength relative to conventional melt or solvent spinning techniques. Reaction spinning involves the formation of filaments from reactive polymers or prepolymers and monomers that are further polymerized and cross-linked during the extrusion process or after the fiber or filament is formed.

Click chemistry refers to a collection of reactions capable of forming a highly reliable molecular connection in solution or bulk state. Click chemistry reactions may be highly selective, high yield reactions which should not interfere with one another as well as other reactions.

It would be desirable to make filaments useful in making surgical devices by extruding a mixture containing first and second precursors functionalized for crosslinking by click chemistry and aided by the process controls of the spinning process, such as temperature, pressure, and time.

SUMMARY

A first aspect of the invention is a method of producing a medical device comprising:

coating a substrate with a polymer possessing a core and at least one functional group known to have click reactivity, whereby a medical device with an activated surface is produced.

In the present application, unless otherwise specified, the expressions 'functional group", "functional group known to have click reactivity" and "reactive member" are used interchangeably to designate a functional group known to have click reactivity.

In the present application, unless otherwise specified, the expression "functionalized polymer" means the polymer possessing the functional group as defined herein.

Another aspect of the invention is a medical device comprising a substrate having a coating, the coating comprising a polymer possessing a functional group having click reactivity.

In embodiments, the substrate is a biocompatible polymeric substrate.

The biocompatible polymeric substrate may include fibers, monofilaments, multifilaments, surgical meshes, ligatures, sutures, staples, patches, slings, foams, pellicles, films, barriers, stents, catheters, shunts, grafts, coil, inflatable balloon and combinations thereof.

The core may be prepared from synthetic materials selected from poly(lactic acid), poly(glycolic acid), poly (lactide), poly(glycolide), poly(trimethylene carbonate), poly(p-dioxanone), polyhydroxybutyrate, polyphosphazine, polyesters, poly(ethylene terephthalate), ultra-high molecular weight polyethylene, poly(ethylene glycol)s, poly(ethylene oxide)s, polyacrylamides, poly(hydroxyethyl methylacrylate), poly(vinylpyrrolidone), poly(vinyl alcohol)s, poly (acrylic acid), polyacetate, polycaprolactone, polypropylene, aliphatic polyesters, glycerols, poly(amino acids), copoly (ether-esters), poly(alkylene oxalate)s, poly (saccharides), polyamides, poly (iminocarbonates), polyoxaesters, polyorthoesters, polyphosphazenes, biopolymers, polymer drugs and copolymers, block copolymers, homopolymers, blends and combinations thereof.

In embodiments, the core may be prepared from natural polymers selected from collagen, cellulose, poly (amino acids), polysaccharides, chitosan and chitosan derivatives (e.g., chitosan acetate/formate polymers), hyaluronic acid, gut, copolymers and combinations thereof.

In embodiments, the functional group known to have click reactivity is selected from the group consisting in an amine, sulfate, thiols, hydroxyl, azides, alkynes, alkenes, carboxyl groups, aldehyde groups, sulfone groups, vinylsulfone groups, isocyanate groups, acid anhydride groups, epoxide groups, aziridine groups, episulfide groups, groups such as $-CO_2N(COCH_2)_2$, $-CO_2N(COCH_2)_2$, $-CO_2H$, $-CHO$, $-CHOCH_2$, $-N=C=O$, $-SO_2CH=CH_2$, $-N(COCH)_2$, $-S-S-(C_5H_4N)$, and/or groups of the following structures wherein X is halogen and R is hydrogen or $C_1$ to $C_4$ alkyl:

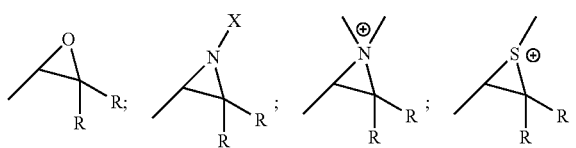

For example, the functional group known to have click reactivity is selected from the group consisting in thiols, azides, alkynes and alkenes.

In particular, the functional group known to have click reactivity may be a thiol. Alternatively, the functional group known to have click reactivity may be an azide. Alternatively, the functional group known to have click reactivity may be an alkyne. Alternatively, the functional group known to have click reactivity may be an alkene.

Implantable medical devices with an activated surface in accordance with this disclosure are fabricated from a substrate having applied thereto a coating including a polymeric material possessing a core and at least one functional group known to have click reactivity. The coating thus provides the implantable medical device with a plurality of functional groups known to have click reactivity at the surface thereof.

DETAILED DESCRIPTION OF EMBODIMENTS

Implantable medical devices in accordance with the present disclosure are prepared from a substrate having applied thereto a coating including a polymeric material possessing a core and at least one functional group known to have click reactivity. The coating thus provides the implantable medical device with a plurality of functional groups known to have click reactivity at the surface thereof.

The Polymeric Substrate

The substrate of the medical devices described herein may be made from any biocompatible polymer. The biocompatible polymer may be a homopolymer or a copolymer, including random copolymer, block copolymer, or graft copolymer. The biocompatible polymer may be a linear polymer, a branched polymer, or a dendrimer. The biocompatible polymer may be bioabsorbable or non-absorbable and may be of natural or synthetic origin.

Examples of suitable biodegradable polymers from which the substrate of the medical devices described herein may be made include, but are not limited to polymers such as those made from alpha-hydroxy acids (e.g. lactic acid, glycolic acid, and the like), lactide, glycolide, ε-caprolactone, δ-valerolactone, carbonates (e.g., trimethylene carbonate, tetramethylene carbonate, and the like), dioxanones (e.g., 1,4-dioxanone), δ-valerolactone, 1,dioxepanones (e.g., 1,4-dioxepan-2-one and 1,5-dioxepan-2-one), ethylene glycol, ethylene oxide, esteramides, hydroxy alkanoates (e.g. γ-hydroxyvalerate, β-hydroxypropionate, 3-hydroxybuterate, and the like), poly (ortho esters), tyrosine carbonates, polyimide carbonates, polyimino carbonates such as poly (bisphenol A-iminocarbonate) and poly (hydroquinone-iminocarbonate), polyurethanes, polyanhydrides, polymer drugs (e.g., polydiflunisol, polyaspirin, and protein therapeutics) and copolymers and combinations thereof. Suitable natural biodegradable polymers include collagen, cellulose, poly (amino acids), polysaccharides, hyaluronic acid, gut, copolymers and combinations thereof.

Examples of suitable non-degradable polymers from which the substrate of the medical devices described herein may be made include, but are not limited to fluorinated polymers (e.g. fluoroethylenes, propylenes, fluoroPEGs), polyolefins such as polyethylene, polyesters such as poly ethylene terepththalate (PET), nylons, polyamides, polyurethanes, silicones, ultra high molecular weight polyethylene (UHMWPE), polybutesters, polyaryletherketone, copolymers and combinations thereof.

The biocompatible polymeric substrate may be fabricated into any desired physical form. The polymeric substrate may be fabricated for example, by spinning, casting, molding or any other fabrication technique known to those skilled in the art. The polymeric substrate may be made into any shape, such as, for example, a fiber, sheet, rod, staple, clip, needle, tube, foam, or any other configuration suitable for a medical device. Where the polymeric substrate is in the form of a fiber, the fiber may be formed into a textile using any known technique including, but not limited to, knitting, weaving, tatting and the like. It is further contemplated that the polymeric substrate may be a non-woven fibrous structure.

The present biocompatible polymeric substrate can be part of any medical device of being implanted at a target location. Some non-limiting examples include fibers, monofilaments, multifilaments, surgical meshes, ligatures, sutures, staples, patches, slings, foams, pellicles, films, barriers, stents, catheters, shunts, grafts, coil, inflatable balloon, and the like. The implantable device can be intended for permanent or temporary implantation.

The Coating

The coating applied to the substrate in accordance with the present disclosure includes a polymer having at least one functional group known to have click reactivity. The polymer used in the coating possesses a core that is functionalized with one or more reactive members.

The core of the polymer may be any suitable biocompatible polymer. The core may be a homopolymer or a copolymer, including random copolymer, block copolymer, or graft copolymer. The core may be a linear polymer, a branched polymer, or a dendrimer. The core of may be a natural material or a synthetic material and may be bioabsorbable or non-bioabsorbable. It should of course be understood that any combination of natural, synthetic, bioabsorbable and non-bioabsorbable materials may be used to form the implantable medical device.

Some non-limiting examples of synthetic materials from which the core may be prepared include, but are not limited to poly(lactic acid), poly(glycolic acid), poly(lactide), poly (glycolide), poly(trimethylene carbonate), poly(p-dioxanone), polyhydroxybutyrate, polyphosphazine, polyesters, poly(ethylene terephthalate), ultra-high molecular weight polyethylene, poly(ethylene glycol)s, poly(ethylene oxide)s, polyacrylamides, poly(hydroxyethyl methylacrylate), poly (vinylpyrrolidone), poly(vinyl alcohol)s, poly(acrylic acid), polyacetate, polycaprolactone, polypropylene, aliphatic polyesters, glycerols, poly(amino acids), copoly (ether-esters), poly(alkylene oxalate)s, poly (saccharides), polyamides, poly (iminocarbonates), polyoxaesters, polyorthoesters, polyphosphazenes, biopolymers, polymer drugs and copolymers, block copolymers, homopolymers, blends and combinations thereof. Suitable natural polymers from which the core may be prepared include collagen, cellulose, poly (amino acids), polysaccharides, chitosan and chitosan derivatives (e.g., chitosan acetate/formate polymers), hyaluronic acid, gut, copolymers and combinations thereof.

In preparing a coating in accordance with the present disclosure, the polymer may be commercially available pre-functionalized cores or may be synthesized. It is contemplated that a plurality of different reactive members may be present and that they may be terminally located, or alternatively located along the length of the polymer chain. In embodiments, the polymer has from about 2 to about 50 reactive members.

Examples of the types of reactions that are known to have click reactivity include cycloaddition reactions. Cycloaddition reactions can be used to form the medical devices, for example fibers, of the present disclosure. These reactions represent highly specific reactant pairs that have a chemoselective nature, meaning that they mainly react with each other and not with other functional members (i.e. different from functional groups and reactive members herein). One example of a cycloaddition reaction is the Huisgen 1,3-dipolar cycloaddition of a dipolarophile with a 1,3 dipolar component that produce five membered (hetero)cycles. Examples of dipolarophiles are alkenes, alkynes, and molecules that possess related heteroatom functional groups, such as carbonyls and nitriles. Specifically, another example is the 2+3 cycloaddition of alkyl azides and acetylenes. Other cycloaddition reactions include Diels-Alder reactions of a conjugated diene and a dienophile (such as an alkyne or alkene).

Other examples of the types of reactions that are known to have click reactivity include a hydrosilation reaction of H—Si and simple non-activated vinyl compounds, urethane formation from alcohols and isocyanates, Menshutkin reactions of tertiary amines with alkyl iodides or alkyl trifluoromethanesulfonates, Michael additions, e.g., the very efficient maleimide-thiol reaction, atom transfer radical addition reactions between —SO2Cl and an olefin ($R^1,R^2$—C=C—$R^3,R^4$), metathesis, Staudinger reaction of phosphines with alkyl azides, oxidative coupling of thiols, many of the procedures already used in dendrimer synthesis, especially in a convergent approach, which require high selectivity and rates, nucleophilic substitution, especially of small strained rings like epoxy and aziridine compounds, carbonyl chemistry like formation of ureas, and addition reactions to carbon-carbon double bonds like dihydroxylation. Therefore, attached functionality may be chosen from acetylene bond, an azido-group, a nitrile group, acetylenic, amino group, phosphino group. The click chemistry reaction may results in the addition of a functional group selected from amino, primary amino, hydroxyl, sulfonate, benzotriazole, bromide, chloride, chloroformate, trimethylsilane, phosphonium bromide or bio-responsive functional group including polypeptides, proteins and nucleic acids, to the polymer.

Thus, suitable reactive members that may be applied to the core include, for example, an amine, sulfate, thiosl, hydroxyl, azides, alkynes, alkenes, carboxyl groups, aldehyde groups, sulfone groups, vinylsulfone groups, isocyanate groups, acid anhydride groups, epoxide groups, aziridine groups, episulfide groups, groups such as —$CO_2N(COCH_2)_2$, —$CO_2N(COCH_2)_2$, —$CO_2H$, —CHO, —$CHOCH_2$, —N=C=O, —$SO_2CH=CH_2$, —$N(COCH)_2$, —S—S—($C_5H_4N$), and/or groups of the following structures wherein X is halogen and R is hydrogen or $C_1$ to $C_4$ alkyl:

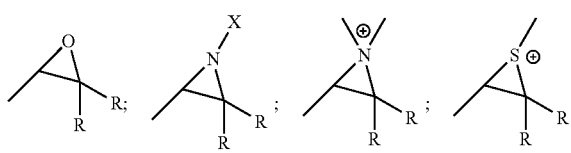

In embodiments, the functional group known to have click reactivity is selected from the group consisting in thiols, azides, alkynes and alkenes.

The core of the polymer can be provided with click reactive members using any variety of suitable chemical processes.

For example, the monomers from which the core is made can be functionalized so that the reactive members appear along the length of the core. In such embodiments, monomers can be initially functionalized with a group such as a halogen to provide a reactive site at which the desired first click reactive member can be attached after polymerization. Thus, for example, a cyclic lactone (e.g., glycolide, lactide, caprolactone, etc.) can be halogenated and then polymerized using known techniques for ring opening polymerization. Once polymerized, the halogenated sites along the resulting polyester chain can be functionalized with a click reactive member, for example, by converting pendant chlorides on the core into azides by reaction with sodium azide. See, R. Riva et al., *Polymer* 49 pages 2023-2028 (2008) for a description of such reaction schemes. Other methods for functionalizing lactones are described in Jerome et al., *Advanced Drug Delivery Reviews,* 60, pages 1056-1076 (2008) and Shi et al., *Biomaterials,* 29, pages 1118-1126 (2008). The entire disclosure of each of these three articles is incorporated herein by this reference. Alternatively, the polymer or copolymer backbone may be halogenated using methods similar to those described by Nottelet et al., *Biomaterials,* 27, pages 4948-4954 (2006). Once halogenated, the backbone can be functionalized with a click reactive functionality by reacting it with a hydroxyacid under condition described by Shi et al. *Biomaterials,* 29, pages 1118-1126 (2008) followed by reaction with sodium azide. The halogen may also be converted directly to the alkyne by reacting it with an alcoholic alkyne such as propargyl alcohol.

Those skilled in the art reading this disclosure will readily envision chemical reactions for activating other core materials to render them suitable for use in coatings in the presently described methods.

Applying the Coating to the Substrate

A composition containing the functionalized polymer described herein can be applied to the substrate employing techniques known to one skilled in the art, e.g., by dipping, wiping, spraying, total immersion, co-extrusion, etc. For example, the coating may be applied by passing the substrate through a solution of the polymer, passing the substrate past a brush or other coating solution applicator, or passing the substrate past one or more spray nozzles dispensing the suture coating solution. The substrate wetted with the coating composition can be passed through or held in a drying oven for a time and at a temperature sufficient to vaporize and drive off the solvent.

The coating composition may take the form of any solution, suspension, semi-solid, or solid material capable of allowing the functionalized polymer to be applied as a coating to the substrate. The polymer may be in granular, pellet, or powder form, or alternatively, may be in a dilute solution. Suitable solvents which may be utilized to form a dilute solution include any biocompatible solvent within the purview of those skilled in the art which will not interfere with the reaction of the reactive members of the first and second precursors. Suitable solvents which may be utilized include, for example, polar solvents such as water, ethanol, triethylene glycol, dimethyl sulfoxide, glymes (such as diglyme, triglyme, tetraglyme, and the like), polyethylene glycols, methoxy-polyethylene glycols, dimethylformamide, dimethylacetamide, gamma-butyrolactone, n-methylpyrollidone, ketones such as methyl ethyl ketone, cyclohexanone, diethylene glycol momethyl ether acetate, diethylene glycol monobutyl ether acetate, diethylene glycol monomethyl ether, diethylene glycol monoethyl ether, diethylene glycol monobutyl ether, diethylene glycol monoisobutyl either, diisobutyl ketone, diacetone alcohol, ethyl amyl ketone, ethyl lactate, and the like. In other embodiments, solvents such as tetrahydrofuran, ethyl acetate, isopropyl acetate, butyl acetate, isopropanol, butanol, acetone, and the like, may be utilized. In embodiments, combinations of any of the foregoing solvents may be utilized to form a dilute solution. The amount of solvent used will depend on a number of factors, including the particular polymer(s) to be employed in the coating composition.

In each case, the resulting coated substrate possesses click reactive functional groups at the surface thereof.

The present medical devices may further be use for delivery of a bioactive agent. Thus, in some embodiments, at least one bioactive agent may be combined with polymer to form the coating composition. The agents may be freely admixed with the functionalized polymer or may be tethered to the polymers through any variety of chemical bonds. In these embodiments, the present devices can also serve as a vehicle for delivery of the bioactive agent. The term "bioactive agent," as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the present devices in any suitable form of matter, e.g., films, powders, liquids, gels and the like.

Examples of classes of bioactive agents which optionally may be utilized in accordance with the coatings of the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesive agents can be used to prevent adhesions from forming between the implantable medical device and the surrounding tissues opposite the target tissue. In addition, anti-adhesive agents may be used to prevent adhesions from forming between the coated implantable medical device and the packaging material. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents which optionally may be included as a bioactive agent in the coating of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the present disclosure.

Other bioactive agents which may be included as a bioactive agent in the coating composition applied in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; antimigraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents which may be included in the coating composition include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

Medical devices having an activated surface in accordance with the present disclosure can be used for a variety of purposes. For example, in embodiments they may be used for drug delivery. In such embodiments, the drug to be delivered is functionalized with one or more reactive members that are complementary to the reactive members in the coating at the surface of the device. By "complementary" it is meant that the reactive members on the drug to be delivered are able to interact with the reactive members in the coating at the surface of the device to covalently bond the drug to be delivered to the surface of the device.

In other embodiments, the medical device having an activated surface in accordance with the present disclosure can be attached to biological tissue by functionalizing tissue with one or more reactive member that are complementary to the reactive members in the coating at the surface of the device. Biological tissue can be provided with reactive member that are complementary to the reactive members in the coating at the surface of the device by conjugation of such groups to various components of tissue such as proteins, lipids, oligosaccharides, oligonucleotides, glycans, including glycosaminoglycans. In embodiments, the complementary groups are attached directly to components of the tissue. In other embodiments, the complementary groups are attached to components of the tissue via a linker. In either case, situating the complementary groups on the tissue can be accomplished by suspending the reactive member in a solution or suspension and applying the solution or suspension to the tissue such that the reactive member bind to a target. The solution or suspension may be poured, sprayed or painted onto the tissue, whereupon the reactive members are incorporate into the tissue.

Those skilled in the art reading this disclosure will readily envision other uses for the activated medical devices described herein.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A method of producing a medical device comprising:
applying a coating composition including a natural polymer possessing a core and at least one functional group known to have click reactivity to a polymeric textile, whereby the coating composition imparts an activated surface to the textile via the functional group having click reactivity and the natural polymer is selected from the group consisting of chitosan, collagen, hyaluronic acid, polysaccharides and copolymers and combinations thereof.

2. The method according to claim 1, wherein the functional group known to have click reactivity is selected from the group consisting in thiols, azides, alkynes and alkenes.

3. The method according to claim 2, wherein the functional group known to have click reactivity is a thiol.

4. The method according to claim 2, wherein the functional group known to have click reactivity is an azide.

5. The method according to claim 2, wherein the functional group known to have click reactivity is an alkyne.

6. The method according to claim 2, wherein the functional group known to have click reactivity is an alkene.

7. The method according to claim 1, wherein the natural polymer comprises chitosan.

8. The method according to claim 1, wherein the polymeric textile is a surgical mesh.

9. The method according to claim 1, wherein the polymeric textile is a sling.

10. The method according to claim 1, wherein applying the coating composition includes dipping, wiping, spraying, total immersion, or co-extrusion.

11. The method according to claim 1, wherein the coating composition comprises a solution or suspension.

12. The method according to claim 1, wherein the coating composition comprises a solvent.

13. The method according to claim 1, further comprising adding a bioactive agent possessing a functional group having click reactivity complementary to the functional group having click reactivity of the coating composition, wherein the bioactive agent covalently bonds to the coating composition.

14. The method according to claim 13, wherein the bioactive agent is selected from the group consisting of anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, muscle relaxants, adrenergic neuron blockers, antineoplastics, immunogenic agents, immunosuppressants, gastrointestinal drugs, diuretics, steroids, lipids, platelet activating drugs, dotting factors, chemotherapeutics and combinations thereof.

15. The method according to claim 1, wherein the polymeric textile comprises a non-absorbable polymer.

16. The method according to claim 1, wherein the polymeric textile comprises an absorbable polymer.

17. The method according to claim 1, wherein the polymeric textile comprises a knit.

18. The method according to claim 1, further comprising knitting a polymeric textile prior to applying the coating composition.

* * * * *